United States Patent
Chalekian et al.

(10) Patent No.: US 8,940,043 B2
(45) Date of Patent: Jan. 27, 2015

(54) AORTIC BANDS

(71) Applicant: St. Jude Medical, Cardiology Division, Inc., St. Paul, MN (US)

(72) Inventors: Aaron J. Chalekian, Savage, MN (US); Paul Edward Ashworth, Wyoming, MN (US); Daniel J. Klima, Andover, MN (US); Catherine A. Pipenhagen, Chanhassen, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 7 days.

(21) Appl. No.: 13/782,049

(22) Filed: Mar. 1, 2013

(65) Prior Publication Data
US 2013/0297009 A1    Nov. 7, 2013

Related U.S. Application Data

(60) Provisional application No. 61/641,513, filed on May 2, 2012.

(51) Int. Cl.
*A61F 2/24* (2006.01)

(52) U.S. Cl.
CPC .............. *A61F 2/2481* (2013.01); *A61F 2/2472* (2013.01)

USPC ........................................... 623/2.36; 623/2.1

(58) Field of Classification Search
CPC ....................................... A61F 2/2481
USPC ........................... 623/2.1, 13.11–13.13, 2.36
See application file for complete search history.

(56) References Cited

U.S. PATENT DOCUMENTS

| 7,601,117 B2 * | 10/2009 | Kute et al. ........................ 600/16 |
| 2004/0133062 A1 * | 7/2004 | Pai et al. ........................... 600/16 |
| 2005/0035635 A1 * | 2/2005 | Hendrikus ..................... 297/250.1 |

\* cited by examiner

*Primary Examiner* — Randy Shay
(74) *Attorney, Agent, or Firm* — Lerner, David, Littenberg, Krumholz & Mentlik, LLP

(57) ABSTRACT

A method of testing the performance of a collapsible prosthetic heart valve includes wrapping an aortic band around an outer surface of a portion of an aorta, fastening a first end portion of the aortic band to a second end portion of the aortic band, implanting a collapsible prosthetic heart valve in the aorta at an implantation site, and flowing a pressurized fluid through the aorta. The aortic band may be positioned near the sinotubular junction of the aorta. When installed around the aorta, the aortic band reinforces the portion of the aorta so as to be more resistant to radial expansion.

9 Claims, 3 Drawing Sheets

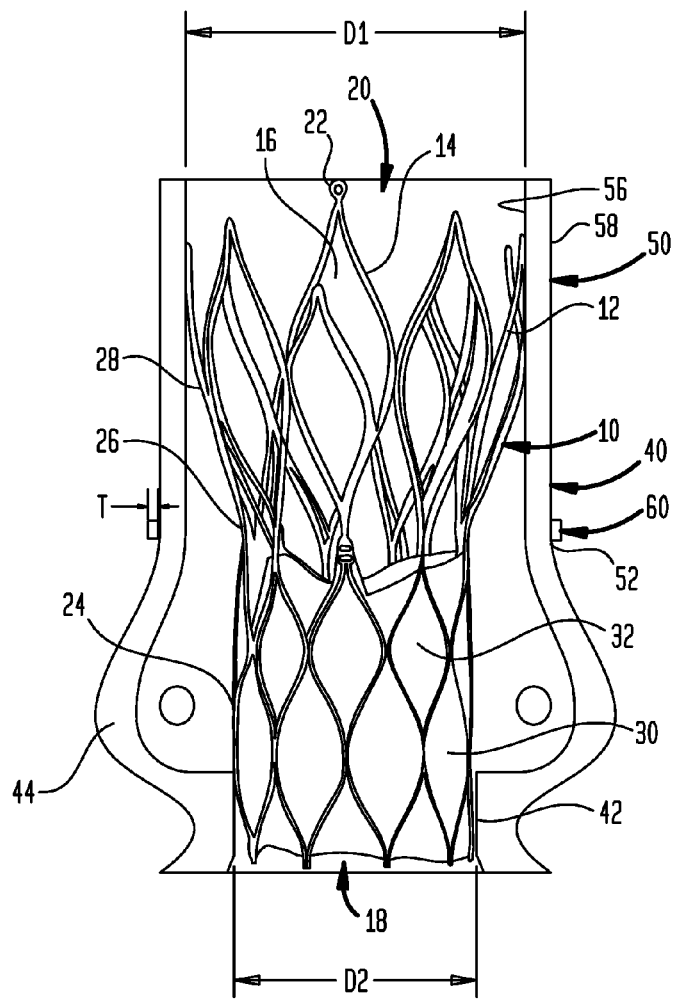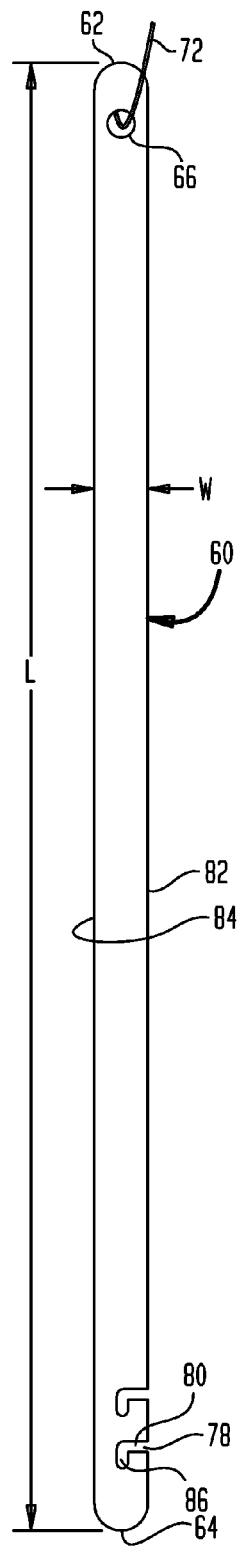

AORTIC BANDS

CROSS-REFERENCE TO RELATED APPLICATION

The present application claims the benefit of the filing date of U.S. Provisional Patent Application No. 61/641,513, filed May 2, 2012, the disclosure of which is hereby incorporated herein by reference.

BACKGROUND OF THE INVENTION

The present invention is related to prosthetic heart valve replacement, and more particularly to devices, systems, and methods for animal testing of prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valves structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically begins to expand as the sheath covering the valve is withdrawn. Once a self-expanding valve has been fully deployed, it expands to a diameter larger than that of the sheath that previously contained the valve in the collapsed condition.

Designs of prosthetic heart valves may be tested in large animals before the designs are used in human patients. Typically, aortic valves are tested in healthy animals that do not have calcific aortic valve stenosis. Such healthy animal aortas may be less resistant to radial expansion than a diseased human aorta, which may result in prosthetic heart valves migrating away from the installed location in a healthy animal aorta.

There therefore is a need for improvements to the devices, systems, and methods for animal testing of prosthetic heart valves. Among other advantages, the present invention may address one or more of these needs.

BRIEF SUMMARY OF THE INVENTION

A method of testing the performance of a collapsible prosthetic heart valve, a method of stiffening a portion of an aorta, and a band assembly for stiffening a portion of an aorta are disclosed.

A method of testing the performance of a collapsible prosthetic heart valve may include inserting a collapsible prosthetic heart valve into an aorta, wrapping an aortic band around an outer surface of the aorta at a position at which the aortic band will circumscribe a portion of the prosthetic heart valve, fastening a first end portion of the aortic band to a second end portion of the aortic band to form a loop of a substantially fixed circumference around the aorta, and flowing a pressurized fluid through the aorta. The aorta may extend in a longitudinal direction.

The method may also include radially expanding the prosthetic heart valve so that the valve exerts an outward radial force that is resisted by the aortic band. The aortic band may be formed of a memory metal biased to a substantially flat condition. The memory metal may be nitinol. The aortic band may be at least partially surrounded by a fabric covering. The step of fastening the first end portion to the second end portion may include connecting the first end portion to the second end portion with a wire. The first end portion of the aortic band may have an aperture extending therethrough. The second end portion of the aortic band may include an L-shaped slot. The step of fastening the first end portion to the second end portion may include connecting one end of the wire to the band through the aperture, passing another end of the wire though the slot, and applying a clip to the another end of the wire. The step of flowing a pressurized fluid through the aorta may be performed while leaflets of the prosthetic heart valve are in a closed position. The method may also include recording a differential pressure across the prosthetic heart valve at which the valve begins to migrate with respect to the aorta in the longitudinal direction of the aorta. The aorta may be a healthy porcine aorta. The aorta may be resected.

A method of stiffening a portion of an aorta may include wrapping an aortic band around an outer surface of the aorta at a position at which the aortic band will circumscribe an ascending aorta portion of the aorta or an aortic root portion of the aorta, and fastening a first end portion of the aortic band to a second end portion of the aortic band to form a loop of a substantially fixed circumference around the aorta.

The aortic band may be formed of a memory metal biased to a substantially flat condition. The aortic band may be at least partially surrounded by a fabric covering. The step of fastening the first end portion to the second end portion may include connecting the first end portion to the second end portion with a wire. The first end portion of the aortic band may have an aperture extending therethrough. The second end portion of the aortic band may include an L-shaped slot. The step of fastening the first end portion to the second end portion may include connecting one end of the wire to the band through the aperture, passing another end of the wire though the slot, and applying a clip to the another end of the wire.

A band assembly for stiffening a portion of an aorta may include an elongated body having a first end portion and a second end portion, an aperture formed in the body in the first end portion, at least one L-shaped slot formed in the body in the second end portion, and a fastener for fastening the first end portion of the band to the second end portion of the band.

The body may be formed of a memory metal biased to a substantially flat condition. The memory metal may be nitinol. A width of the band may be between about 0.05" and about 0.15", and a thickness of the band may be between about 0.002" and about 0.008". Each L-shaped slot may have an entry leg extending from a first elongated edge of the body towards a second elongated edge of the body and a capture leg extending a distance from the entry leg in a longitudinal direction of the body.

The band assembly may also include a fabric covering at least partially surrounding the body. The fabric covering may be a polyester material. The fastener may include a wire connected to the body through the aperture and adapted to fasten the first end portion to the second end portion. One end of the wire may be connected to the body through the aperture. The fastener may also include a clip adapted to be applied to another end of the wire extending through one of the L-shaped slots.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 2 is a diagrammatic longitudinal cross-sectional view of the ascending aorta of FIG. 1 with the aortic band of FIG. 1 installed thereon;

FIG. 3 is a plan view of the aortic band of FIG. 2, shown in a flat condition;

DETAILED DESCRIPTION

As used herein, the terms "proximal" and "distal" are to be taken as relative to a user (e.g., a surgeon, a researcher, or an interventional cardiologist) using the aortic band. "Proximal" is to be understood as relatively close to the user and "distal" is to be understood as relatively farther away from the user.

The aortic bands of the present invention are primarily intended for use to enable testing of the functionality and the stability of a prosthetic valve in typical or extreme conditions, for example, during pressure dislodge testing of the valve. Such testing may be performed using the resected aorta of a healthy animal, or using the aorta of a healthy living animal, in which an aortic band according to the present invention may be installed. The aorta of a healthy animal may be less resistant to radial expansion than a stenosed human aorta. Accordingly, the aortic bands have been designed to mimic the resistance of a calcified aorta, and thereby facilitate testing by preventing migration of a valve implanted in a healthy animal aorta at pressures that are significantly below the pressure at which the valve would migrate in a calcified human aorta.

Figure 1:
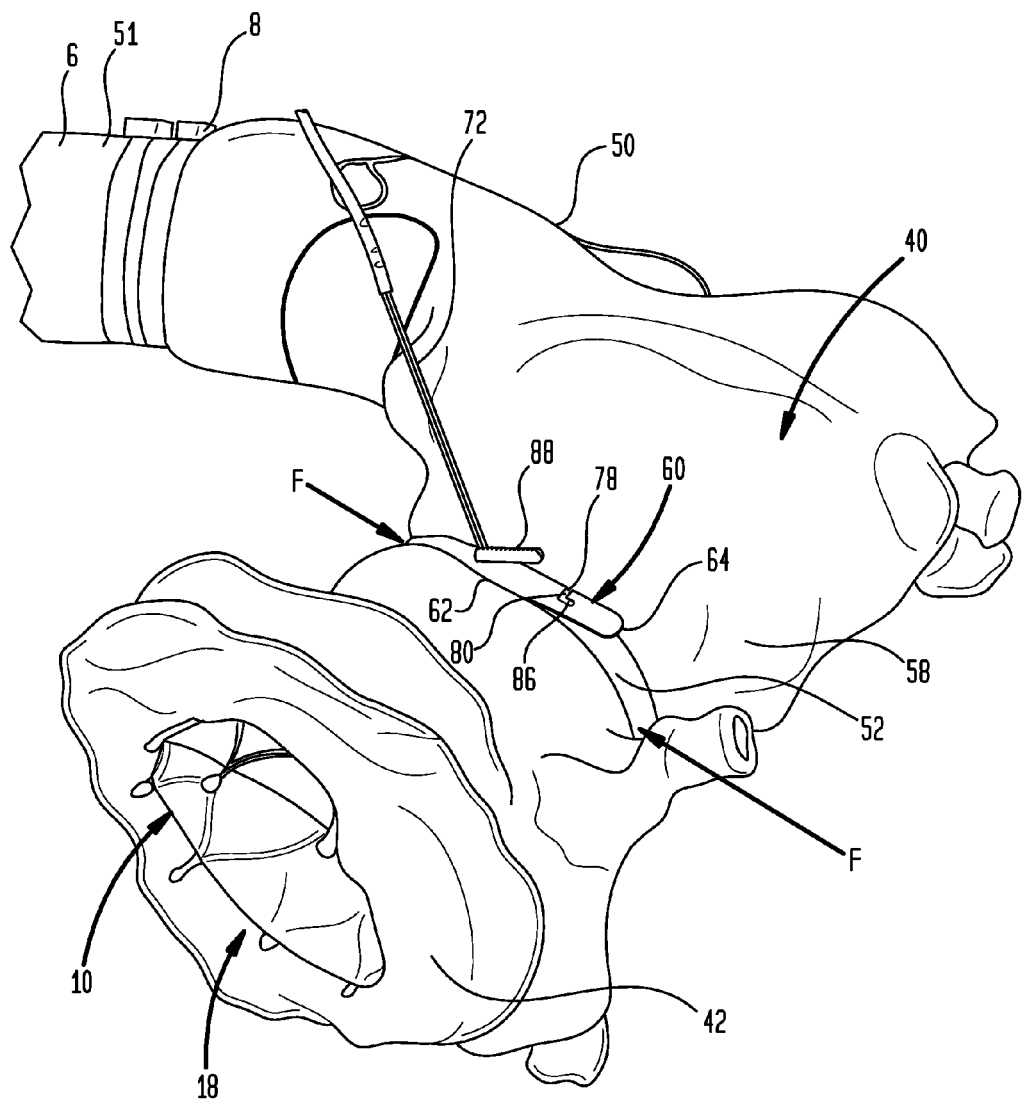
FIG. 1 is a perspective view of a resected aorta with one embodiment of an aortic band installed thereon.

Referring to FIGS. 1 and 2, a collapsible prosthetic valve 10 is shown implanted within a resected aorta 40. The aorta 40 may be resected from the heart of a pig or any other animal just below the native annulus 42 of the aorta, such that the native annulus remains attached to the aorta. The aorta 40 may be resected from a healthy animal so that testing may be performed on a prosthetic valve such as the collapsible prosthetic valve 10 in a tissue environment that may have dimensions similar to a human aorta.

The valve 10 is adapted to be movable between an expanded condition shown in FIG. 2 and a collapsed condition in which the valve is radially compressed to fit into a compartment of a valve delivery device. The valve 10 includes a stent portion 12 having a valve end 18, an aortic end 20, and a plurality of stent members 14 defining open cells 16 therebetween. A plurality of retention members 22 provided at the aortic end 20 of the stent portion 12 are adapted to engage with a retainer of a valve delivery device to retain the valve 10 during the deployment process. Examples of suitable retainers and methods of coupling prosthetic valves to such retainers are shown and described in co-pending application No. 61/364,453, filed on Jul. 15, 2010, the disclosure of which is hereby incorporated by reference herein. The description that follows assumes that the valve 10 is a self-expanding prosthetic valve. In such cases, the stent members 14 may be formed of a memory metal material, such as nitinol, so that the valve 10 may have a memory bias towards the expanded condition.

When the valve 10 is in the expanded condition and implanted within the aorta 40, the stent portion 12 may taper in diameter from a diameter D1 at the aortic end 20 to a diameter D2 at the valve end 18, the diameter D1 being greater than the diameter D2. The stent portion 12 may have a valve section 24 that has a substantially constant diameter D2 from the valve end 18 to a transition boundary 26. The stent portion 12 also may have an aortic section 28 that gradually increases in diameter from the diameter D2 at the transition boundary 26 to the diameter D1 at the aortic end 20.

A tissue cuff 30 may extend circumferentially about at least a portion of the inner and/or outer surface of the valve section 24, and three leaflets 32 may extend inwardly from the tissue cuff.

The valve 10 may be implanted with the valve section 24 positioned in the native annulus 42, the aortic end 20 extending into the ascending aorta 50, preferably above the aortic root 44, and the transition boundary 26 positioned near the sinotubular junction 52.

The aortic end 20 of the valve 10 may have a maximum diameter in a radially unconstrained state that is greater than the diameter D1 of the aortic end when implanted in the ascending aorta 50, such that the memory bias of the stent portion will provide a radially-outward force against an inner surface 56 of the ascending aorta. Likewise, the valve section 24 of the valve 10 may have a maximum diameter in a radially unconstrained state that is greater than the diameter D2 of the valve end 18 when implanted in the native annulus 42, with the memory bias of the stent portion providing a radially-outward force against the native annulus.

As seen in FIGS. 1 and 2, an aortic band 60 is installed around an outer surface 58 of the resected aorta 40. The band 60 may be positioned between the valve end 18 and the aortic end 20 of the valve 10, preferably near the sinotubular junction 52.

Referring to FIG. 3, the aortic band 60 has a length L defined between a first end 62 and a second end 64. A wire 72 may be connected to the band 60 through an aperture 66 provided adjacent the first end 62. The wire 72 may, for example, be a suture or a stranded stainless steel cable having a diameter of about 0.007". The wire 72 may have a large knot (not shown) formed in one end with a diameter greater than the diameter of the aperture 66, thereby preventing the knot from pulling through the aperture. Other arrangements for securing the wire 72 to the aperture 66 are also contemplated herein.

The band 60 includes one or more L-shaped slots 78 adjacent the second end 64, each slot being sized to receive the wire 72. Each slot 78 has an entry leg 80 extending from a first elongated edge 82 of the band 60 partially through the width W of the band, and a capture leg 86 extending from the entry leg in a direction substantially perpendicular to the entry leg toward the second end 64. The band 60 may be formed from a memory metal material, such as nitinol, so that the band may have a memory bias towards the flat condition shown in FIG. 3. In an exemplary embodiment, the band 60 may have a width W between about 0.05" and 0.15" and a thickness T between about 0.002" and 0.008". In one example, the band 60 may have a width W of about 0.100" and a thickness T of about 0.005".

In use, the aortic band 60 may be installed around the outer surface 58 of the aorta 40 near the sinotubular junction 52. This may be accomplished by placing a flat surface of the band 60 against the outer surface 58 of the aorta 40 and wrapping the band around the outer surface of the aorta until the first end 62 and the second end 64 are located near one another, thereby disposing the band in a looped condition.

Once properly positioned, the band 60 may be held in the looped condition by securing the first end 62 to or adjacent to the second end 64. To do this, the user may grasp a free end of the wire 72 and pass it through one of the L-shaped slots 78. The memory bias of the band 60 towards the flat condition shown in FIG. 3 may cause the wire 72 to slide into the capture leg 86 of the L-shaped slot 78, thereby preventing the wire from slipping out of the L-shaped slot through the entry leg 80. The user may fasten the first end 62 of the band 60 to the second end 64 by installing one or more clips 88 on the wire 72 at the location where the wire passes through the L-shaped slot 78. The clip 88 may be, for example, a titanium ligating clip. When fastened around the outer surface 58 of the aorta 40, the band 60 may provide a radially-inward force F (FIG. 1) tending to tighten the inner surface 56 of the ascending aorta 50 against the valve 10.

During pressure dislodge testing of the prosthetic valve 10, a healthy resected porcine aorta 40 with an aortic band 60 installed thereabout may approximate the stiffness of a stenosed human aorta. That is, the "banded" porcine aorta may more closely approximate the resistance to radially-outward expansion of a stenosed human aorta than would a resected porcine aorta without such a band, so that pressure dislodge testing of such a healthy banded porcine aorta may produce a similar dislodgement pressure as a stenosed human aorta.

Pressure dislodge testing of the prosthetic valve 10 may be performed, for example, by implanting the valve in the resected aorta 40 of a healthy porcine heart. A liquid such as saline may be forced into the ascending portion 50 of the resected aorta 40 through an inlet tube 6 that may be attached to an end 51 of the ascending aorta by one or more attachment bands 8. The liquid may apply pressure against the valve 10 with the leaflets thereof in the closed position, and the differential pressure across the valve at which the valve is dislodged from the native annulus 42 may be measured.

A healthy resected porcine aorta 40 may have an inner surface 56 that has less resistance to radially-outward expansion under liquid pressure inside the aorta than the inner surface of a human aorta that has become stenosed. Pressure dislodge testing of such a healthy porcine resected aorta 40 may produce a lower differential pressure across the valve at which the valve 10 is dislodged from the native annulus 42 than would result for a calcified human aorta.

Positioning the aortic band 60 near the sinotubular junction 52 of the ascending aorta 50, such that the aortic band is located near the transition boundary 26 of the valve 10 may provide extra stiffness to the inner surface 56 of the aorta near the transition boundary. In an embodiment in which the aortic end 20 of the valve 10 has a maximum diameter in a radially unconstrained state that is greater than its diameter when implanted in the ascending aorta 50, such that the memory bias of the stent portion 12 will provide a radially-outward force against the inner surface 56 of the ascending aorta, the aortic band 60 may constrain the aorta such that its inner surface is less than the unconstrained maximum diameter of the aortic end of the valve. Such extra stiffness applied to the ascending aorta 50 near the transition boundary 26 may help prevent the aortic section 28 of the valve 10 from migrating proximally towards the native annulus 42 when a pressurized liquid is applied to the valve from the aortic end 20.

Figure 4:
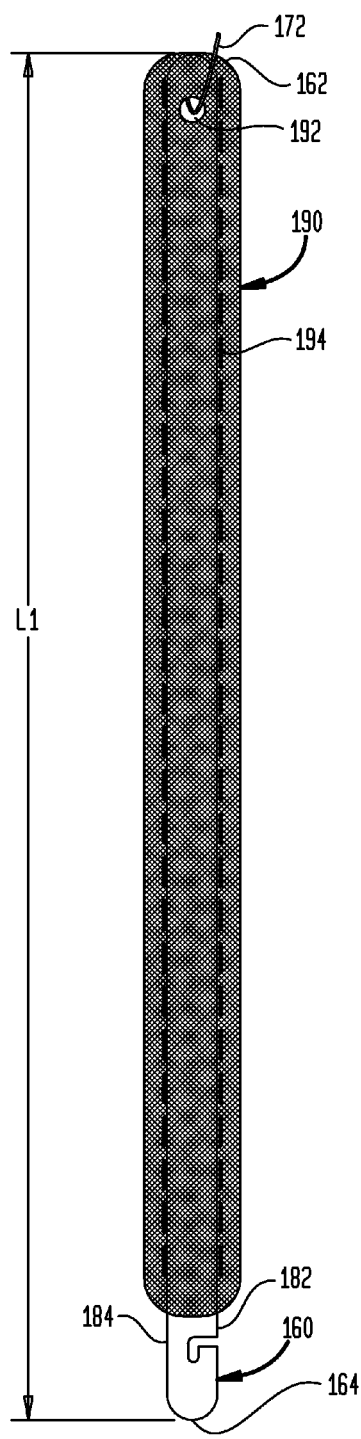
FIG. 4 is a plan view of another embodiment of an aortic band, shown in a flat condition.
Figure 5:
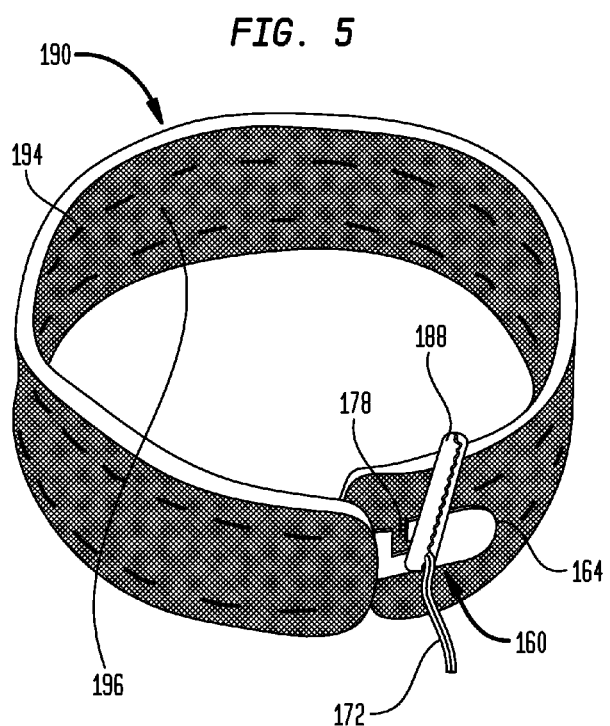
FIG. 5 is a perspective view of the aortic band of FIG. 4, shown in a use condition.

FIGS. 4 and 5 illustrate an alternate embodiment of the aortic band 60 shown in FIG. 3. The aortic band 160 shown in FIGS. 4 and 5 is the same as the aortic band 60 described above, except that a fabric covering 190 surrounds the aortic band 160 from the first end 162 along all or most of the length L1 of the band. The fabric covering 190 may be secured around the aortic band 160 by a wire 172 extending through an aperture 192 formed in the fabric covering coextensively with an aperture 166 formed in the band, and by attachment wires in the form of sutures 194 extending through the fabric covering adjacent the first and second edges 182 and 184 of the band. In an exemplary embodiment, the fabric covering 190 may be made from a polyester fabric, and the sutures 194 may be 5-0 polyester sutures. Alternatively, the covering 190 may be made of a material other than fabric, such as a polymer coating surrounding a metal band 160.

As can be seen in FIG. 5, when the aortic band 160 is in the looped condition with the wire 172 extending through one of the L-shaped slots 178 and fastened to the second end 164 with the clip 188, an inner surface 196 of the fabric covering 190 may extend around the entire inwardly-directed portion of the circumference of the band 160, such that, when installed around an aorta 40 (FIG. 1), the metal material of the band 160 will not directly contact the outer surface 58 of the aorta 40.

Although the various aortic bands have been described herein as being fastened around the aorta near the sinotubular junction, all of the aortic bands described above may be installed around other parts of the aorta, including the ascending aorta above the sinotubular junction or the aortic root below the sinotubular junction.

The aortic bands have been described above as being made of a flat sheet of metal or metal surrounded by a fabric covering, but the invention also contemplates the use of any other suitable material or combination of materials for the aortic bands. For example, the aortic band may be made of a flat sheet of a polymer or a braided metal or polymer material, with or without a covering.

Furthermore, although the various aortic bands have been described herein as having their ends fastened together with a wire and a clip, any other suitable mechanism may be used to fasten the ends of the aortic band together. In particular examples, the two opposing ends of the aortic band may be fastened to one another by the use of a snap feature, an interlocking joining feature, hook and loop fasteners, or an adhesive extending between the two ends of the bands.

Although the various aortic bands have been described herein in connection with the deployment of a prosthetic aortic valve having a collapsible stent structure, all of the aortic bands described above may be used to stiffen the aorta for testing of other types of aortic valves or to stiffen other animal tissue structures, such as a carotid artery. For example, the aortic band 60 or 160 may be used for implantation or testing of a balloon-expandable prosthetic valve, in which the stent members may be formed of a material that is plastically deformable. In particular embodiments, the aortic bands described above may be used to stiffen animal tissue structures for implantation or testing of conventional collapsible stents or other prosthetic devices that do not contain a valve.

Although the invention herein has been described with reference to particular embodiments, it is to be understood that these embodiments are merely illustrative of the principles and applications of the present invention. For example, while the aortic bands of the present invention have been described in connection with their use to reinforce a healthy resected aorta for pressure dislodge testing, in other examples, the aortic band 60 or 160 may be installed around any other animal tissue to provide increased stiffness thereto for any other purpose. For example, the aortic band 60 or 160 may be installed around an aorta of a living animal to provide increased stiffness to the aorta. In such an example, the aorta would not be resected, and the aortic band 60 or 160 may be installed around the aorta of the living animal, for example, near the sinotubular junction. The aortic band 60 or 160 may be installed around the aorta of the living animal before or after insertion of a prosthetic valve into the native annulus. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A band assembly for stiffening a portion of an aorta, the band assembly comprising:
    an elongated body having a first end portion and a second end portion, the body forming a loop in an assembled condition, the body being biased toward a substantially flat condition;
    an aperture formed in the body in the first end portion;
    at least one L-shaped slot formed in the body in the second end portion; and
    a fastener for fastening the first end portion of the band to the second end portion of the band.

2. The band assembly of claim 1, wherein the body is formed of a memory metal.

3. The band assembly of claim 2, wherein the memory metal is nitinol.

4. The band assembly of claim 1, wherein a width of the band is between 0.05" and 0.15" and a thickness of the band is between 0.002" and 0.008".

5. The band assembly of claim 1, wherein each L-shaped slot has an entry leg extending from a first elongated edge of the body towards a second elongated edge of the body and a capture leg extending a distance from the entry leg in a longitudinal direction of the body.

6. The band assembly of claim 1, further comprising a fabric covering at least partially surrounding the body.

7. The band assembly of claim 6, wherein the fabric covering is a polyester material.

8. The band assembly of claim 1, wherein the fastener includes a wire connected to the body through the aperture and adapted to fasten the first end portion to the second end portion.

9. The band assembly of claim 8, wherein one end of the wire is connected to the body through the aperture, the fastener further including a clip adapted to be applied to another end of the wire, the another end of the wire extending through one of the at least one L-shaped slot.

* * * * *